United States Patent
Brtko et al.

(10) Patent No.: US 7,790,920 B2
(45) Date of Patent: Sep. 7, 2010

(54) PREPARATION OF ACETIC ACID

(75) Inventors: Wayne J. Brtko, Glen Mills, PA (US); Michael E. Fitzpatrick, League City, TX (US); Brian A. Salisbury, Oxford, PA (US)

(73) Assignee: Lyondell Chemical Technology, L.P., Wilmington, DE (US)

( * ) Notice: Subject to any disclaimer, the term of this patent is extended or adjusted under 35 U.S.C. 154(b) by 16 days.

(21) Appl. No.: 12/283,329

(22) Filed: Sep. 11, 2008

(65) Prior Publication Data
US 2010/0063319 A1    Mar. 11, 2010

(51) Int. Cl.
*C07C 51/12* (2006.01)
*C07C 51/14* (2006.01)
(52) U.S. Cl. ....................... 562/519; 562/517
(58) Field of Classification Search ............... 562/519, 562/517
See application file for complete search history.

(56) References Cited

U.S. PATENT DOCUMENTS

| | | | |
|---|---|---|---|
| 4,039,395 A | 8/1977 | Eby | |
| 5,817,869 A | 10/1998 | Hinnenkamp et al. | |
| 5,932,764 A | 8/1999 | Morris et al. | |

FOREIGN PATENT DOCUMENTS

WO    WO 2007/007891    1/2007

*Primary Examiner*—Taylor Victor Oh
(74) *Attorney, Agent, or Firm*—Shao-Hua Guo

(57) ABSTRACT

A process for producing acetic acid is disclosed. The process comprises carbonylating methanol to form a reaction mixture comprising a catalyst, catalyst stabilizer, acetic acid, methanol, methyl iodide, methyl acetate, water, and carbon monoxide and introducing at least a portion of the reaction mixture to a distillation column to separate into a bottom steam comprising the catalyst and catalyst stabilizer, a sidedraw stream comprising acetic acid and water, and an overhead stream comprising methanol, methyl acetate, methyl iodide, and water. The process of the invention eliminates the use of flash tank.

14 Claims, 1 Drawing Sheet

PREPARATION OF ACETIC ACID

FIELD OF THE INVENTION

Figure 1:
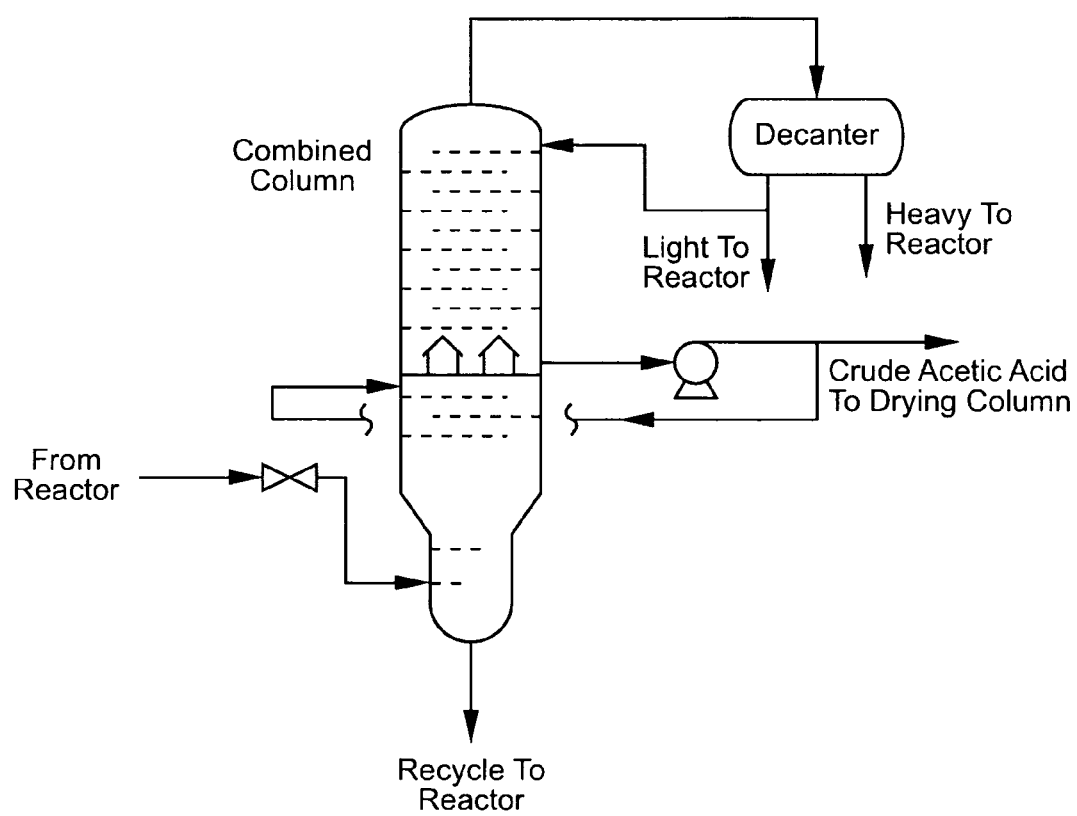

The invention relates to the preparation of acetic acid by methanol carbonylation. More particularly, the invention relates to an acetic acid production process which eliminates the use of flash tank.

BACKGROUND OF THE INVENTION

Production of acetic acid by methanol carbonylation is known. See U.S. Pat. No. 5,817,869. In the current acetic acid production process, a reaction mixture is withdrawn from the reactor and is separated by a flash tank into a liquid fraction comprising the catalyst and the catalyst stabilizer and a vapor fraction comprising the acetic acid product, the reactants, water, methyl iodide, and impurities generated during the carbonylation reaction. The liquid fraction is then recycled to the carbonylation reactor. The vapor fraction is then passed to a so-called "light-ends distillation." The light-ends distillation separates acetic acid from other components.

The light ends distillation separates an overhead fraction comprising methyl iodide, water, methanol, and methyl acetate from an acetic acid stream comprising acetic acid, a small amount of water, and heavy impurities. The acetic acid stream is passed to a drying column to remove water and then be subjected to a so called "heavy-ends distillation" to remove the heavy impurities such as propionic acid.

One problem associated with the current process is that the catalyst, usually expensive rhodium or iridium metals, cannot be completely recovered because it is entrained in the vapor phase or affixed on the wall of the flash tank.

Another problem associated with the current process is that the catalysts are often deactivated during the flashing. Rhodium and iridium catalysts need a high concentration of water to stabilize. During flashing, a significant amount of water goes with the vapor phase, and thus the rhodium and iridium catalysts become unstable due to lack of sufficient water.

Further, equipment for acetic acid production requires high corrosion resistance. The flash tank is often constructed of corrosion resistant metals such as Hastelloy B-2 and Zirconium 702. These metals are very expensive.

A new process for producing acetic acid is needed. Ideally, the process would eliminate the flash tank.

SUMMARY OF THE INVENTION

The invention is a process for producing acetic acid. The process comprises carbonylating methanol to form a reaction mixture comprising a catalyst, catalyst stabilizer, acetic acid, methanol, methyl iodide, methyl acetate, water, and carbon monoxide, and introducing at least a portion of the reaction mixture to a distillation column to separate into a bottom steam comprising the catalyst and catalyst stabilizer, a sidedraw stream comprising acetic acid and water, and an overhead stream comprising methanol, methyl acetate, methyl iodide, and water. The process of the invention eliminates the use of flash tank.

DETAILED DESCRIPTION OF THE INVENTION

The process of the invention comprises carbonylating methanol. The carbonylation reaction is performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The carbonylation reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The carbonylation reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydrolysis or methanolysis of polyvinyl acetate can be 1o used for the carbonylation reaction.

The carbonylation reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic acid reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 1,000 psig. More preferably, the reaction is performed under a pressure within the range of about 300 psig to about 500 psig.

The reaction mixture is withdrawn from the reactor and, instead of entering a flash tank, is sent directly to a distillation column to separate into at least three streams: a bottom liquid stream, a sidedraw liquid stream, and an overhead vapor stream.

Preferably, the distillation column has at least 10 actual stages. More preferably, the distillation column has at least 14 actual stages. Most preferably, the distillation column has at least 18 actual stages. One actual stage equals approximately to 0.6 theoretical stage. Actual stages can be trays or packing. The reaction mixture is fed to the distillation column at the bottom or the first stage of the column.

The distillation column is preferably operated at an overhead pressure within the range of 20 psia (1.4 kg/cm$^2$) to 40 psia (2.8 kg/cm$^2$). More preferably, the overhead pressure is within the range of 25 to 35 psia. Preferably, the overhead temperature is within the range of 95° C. to 135° C. More preferably, the overhead temperature is within the range of 100° C. to 125° C. Most preferably, the overhead temperature is within the range of 110° C. to 120° C. This overhead vapor comprises water, carbon monoxide, carbon dioxide, methyl iodide, methyl acetate, methanol and acetic acid.

The distillation column is preferably operated at a bottom pressure within the range of 25 psia to 45 psia. More preferably, the bottom pressure is within the range of 30 psia to 40 psia. Preferably, the bottom temperature is within the range of 115° C. to 155° C. More preferably, the bottom temperature is within the range of 125° C. to 135° C. The bottom stream comprises the catalyst, catalyst stabilizer, acetic acid and water.

A liquid sidedraw is preferably operated at a pressure within the range of 25 psia to 45 psia. More preferably, the sidedraw pressure is within the range of 30 psia to 40 psia. Preferably, the sidedraw temperature is within the range of 110° C. to 140° C. More preferably, the sidedraw temperature is within the range of 120° C. to 130° C. The sidedraw is preferably taken between the fifth to the eighth stage. The sidedraw stream is a crude acetic acid which comprises acetic acid, water and impurities such as propionic acid.

The overhead stream from the distillation column is preferably condensed and separated in a decanter to a light, aqueous phase and a heavy, organic phase. The heavy, organic phase comprises methyl iodide and methyl acetate. The light, aqueous phase comprises predominantly water (greater than 50%), acetic acid, and methyl acetate. The aqueous phase refluxes the top of the distillation column or a portion of it is optionally recycled to the carbonylation reaction.

The sidedraw stream is optionally subjected to further purification such as drying-distillation to remove water and heavy-ends distillation to remove heavy lo impurities such as propionic acid.

The following example merely illustrates the invention. Those skilled in the art will recognize many variations that are within the spirit of the invention and scope of the claims.

EXAMPLE

This process of the invention is modeled by Aspen Plus and the results are as follows. As shown in FIG. 1, a carbonylation mixture (100 parts by weight) comprising water 6.37%, carbon monoxide 0.13%, carbon dioxide 0.09%, hydrogen iodide 2.70%, methyl iodide 12.91%, methyl acetate 2.85%, methanol 0.02%, acetic acid 65.57%, propionic acid 0.04%, a catalyst stabilizer 9.28%, and a catalyst 0.04% is fed to a distillation column at stage 1. The distillation column has 11 theoretical stages or 18 actual stages.

The distillation column overhead is at 32.7 psia and 116° C. The overhead vapor (20.6 parts by weight) comprises water, carbon monoxide, carbon dioxide, methyl iodide, methyl acetate, methanol and acetic acid. The overhead stream is cooled to 38° C. and condensate flows to a decanter for liquid separation.

The resulting decanter heavy phase (12.8 parts by weight), which comprises water 0.46%, carbon monoxide 0.02%, carbon dioxide 0.27%, methyl iodide 88.83%, methyl acetate 8.34% and acetic acid 2.08%, recycles to the reactor. A portion of the light phase (1.8 parts by weight), which comprises water 54.15%, carbon dioxide 0.09%, methyl iodide 3.43%, methyl acetate 8.03%, methanol 0.36% and acetic acid 33.94%, also recycles to the reactor. The remainder of the light phase (6.3 parts by weight) is refluxed to the top of the distillation column.

The distillation column bottom operates at 35.4 psia and 132° C. The bottom stream (67.5 parts by weight) comprises water 5.58%, carbon monoxide 0.04%, carbon dioxide 0.30%, hydrogen iodide 3.99%, methyl iodide 1.23%, methyl acetate 1.84%, methanol 0.01%, acetic acid 73.18%, propionic acid 0.05%, catalyst stabilizer 13.72% and catalyst 0.06%. This stream recycles to lo the reactor.

A liquid sidedraw (19.1 parts by weight) at 34.9 psia and 127° C. is taken from the sixth stage counting from the bottom of the distillation column. This stream comprises water 8.82%, hydrogen iodide 0.04%, methyl iodide 3.80%, methyl acetate 2.22%, methanol 0.02%, acetic acid 85.06% and propionic acid 0.04%. The majority (94%) of the stream is a crude acetic acid which flows to downstream equipment for drying and recovery of pure acetic acid. The remaining 6% of the stream refluxes in the section of the distillation column below the liquid sidedraw.

We claim:
1. A process for producing acetic acid, said process comprising:
  (a) carbonylating methanol in the presence of a catalyst selected from the group consisting of rhodium catalysts and iridium catalysts, catalyst stabilizer, water and methyl iodide to form a reaction mixture comprising the catalyst, catalyst stabilizer, acetic acid, methanol, methyl iodide, methyl acetate, and water; and

(b) withdrawing the reaction mixture and feeding it to a distillation column to separate into a bottom stream comprising the catalyst and catalyst stabilizer, a sidedraw stream comprising acetic acid and water, and an overhead stream comprising methanol, methyl acetate, methyl iodide, and water; wherein no flash tank is used between steps (a) and (b).

2. The process of claim 1, wherein the bottom stream of step (b) is recycled to the carbonylation of step (a).

3. The process of claim 1, wherein the overhead stream of step (b) is recycled to the carbonylation of step (a).

4. The process of claim 1, wherein the overhead stream is phase-separated to a light, aqueous phase comprising water, acetic acid, and methyl acetate and a heavy, organic phase comprising methyl iodide and methyl acetate.

5. The process of claim 4, wherein the heavy, organic phase is recycled to the carbonylation of step (a).

6. The process of claim 4, wherein the light, aqueous phase is recycled to the distillation of step (b) or to the carbonylation of step (a).

7. The process of claim 1, further comprising distilling the sidedraw stream to remove water.

8. The process of claim 1, wherein the catalyst is a rhodium catalyst.

9. The process of claim 8, wherein the catalyst stabilizer is selected from the group consisting of pentavalent Group VA oxides, metal iodide salts, and mixtures thereof.

10. The process of claim 8, wherein the catalyst stabilizer is a phosphine oxide.

11. The process of claim 8, wherein the catalyst stabilizer is triphenylphosphine oxide.

12. The process of claim 8, wherein the catalyst stabilizer is a metal iodide salt.

13. The process of claim 8, wherein the catalyst stabilizer is lithium iodide.

14. The process of claim 1, wherein the concentration of water in step (a) is up to 10 wt % of the reaction mixture.

* * * * *